United States Patent [19]

Toya et al.

[11] 4,284,717
[45] Aug. 18, 1981

[54] SILVER HALIDE PHOTOGRAPHIC EMULSION

[75] Inventors: Ichizo Toya; Yoshiharu Fuseya, both of Minami-ashigara, Japan

[73] Assignee: Fuji Photo Film Co., Ltd., Minami-ashigara, Japan

[21] Appl. No.: 100,161

[22] Filed: Dec. 4, 1979

[30] Foreign Application Priority Data

Dec. 7, 1978 [JP] Japan .................................. 53/151594

[51] Int. Cl.³ .......................... G03C 1/02; G03C 1/28
[52] U.S. Cl. .................................... 430/567; 430/569; 430/570; 430/596; 430/603; 430/604
[58] Field of Search ............... 430/567, 569, 596, 603, 430/455, 604, 570

[56] References Cited

U.S. PATENT DOCUMENTS

| | | | |
|---|---|---|---|
| 2,410,689 | 11/1946 | Sheppard et al. | 430/603 |
| 3,287,137 | 11/1966 | McBride | 430/603 |
| 3,320,069 | 5/1967 | Illingsworth | 430/603 |
| 3,364,032 | 1/1968 | Jones | 430/567 |
| 3,773,516 | 11/1973 | Gutoff | 430/567 |
| 3,817,756 | 6/1974 | Claes et al. | 430/567 |
| 4,067,739 | 1/1978 | Lewis | 430/567 |
| 4,184,878 | 1/1980 | Maternaghan | 430/567 |

*Primary Examiner*—J. Travis Brown

*Attorney, Agent, or Firm*—Sughrue, Rothwell, Mion, Zinn and Macpeak

[57] ABSTRACT

A silver halide photographic emulsion containing silver halide grains formed in the presence of a silver halide solvent of the formula (I):

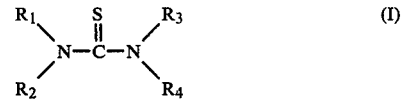

wherein $R_1$, $R_2$, $R_3$ and $R_4$ are each a subtituted or unsubstituted alkyl group, a substituted or unsubstituted alkenyl group (e.g., allyl group), a substituted or unsubstituted aryl group or a substituted or unsubstituted nitrogen-containing heterocyclic ring; or $R_1$ and $R_2$, $R_2$ and $R_3$, and $R_3$ and $R_4$ when taken together may form a 5- or 6-membered heterocyclic ring; provided at least one of R to $R_4$ is a 5- or 6-membered nitrogen-containing heterocyclic ring, an alkyl group or aryl group substituted with an amino group, an alkyl grop substituted with a nitrogen-containing heterocyclic ring, or $R_1$ and $R_2$, $R_2$ and $R_3$, or $R_3$ and $R_4$ combine to form a 5- or 6-membered nitrogen-containing heterocyclic ring containing at least two nitrogen atoms.

22 Claims, No Drawings

SILVER HALIDE PHOTOGRAPHIC EMULSION

BACKGROUND OF THE INVENTION

1. Field of the Invention

This invention relates to a novel silver halide emulsion.

2. Description of the Prior Art

It has been difficult to prepare uniformly shaped silver halide grains with narrow size distribution in a low pBr (high pAg) region by the conventional method using ammonia as a silver halide solvent. To produce silver halide cubes with narrow grain size distribution by such conventional method, strict control of pAg is required in a high pBr (low pAg) region but this is very difficult to achieve. As is well known to those skilled in the art, the preparation of cubic silver halide crystals is very advantageous for increasing the efficiency of the spectral sensitization of a silver halide photographic emulsion and is therefore effective for providing a high-sensitivity photographic emulsion. This is why there is a demand in the photographic industry for a silver halide solvent that is capable of providing uniformly shaped silver halide grains of narrow size distribution even in a low pBr (high pAg) region, particularly, for a silver halide solvent that can provide cubic silver halide grains of narrow size distribution even in a low pBr (high pAg) region.

SUMMARY OF THE INVENTION

Therefore, one object of this invention is to provide a photographic emulsion which contains uniformly shaped silver halide grains of narrow size distribution in a low pBr (high pAg) region.

Another object of this invention is to provide a photographic emulsion which contains silver halide grains having a (100) plane and narrow size distribution in a low pBr (high pAg) region.

A further object of this invention is to provide a process for preparing a silver halide photographic emulsion which contains silver halide grains having a (100) plane and narrow size distribution in a low pBr region.

It has been found that the above objects of the present invention are achieved by preparing silver halide grains in the presence of a silver halide solvent of the formula (I):

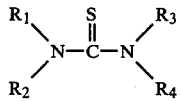

wherein $R_1$, $R_2$, $R_3$ and $R_4$ are each a substituted or unsubstituted alkyl group, a substituted or unsubstituted alkenyl group (e.g., allyl group), a substituted or unsubstituted aryl group or a substituted or unsubstituted nitrogen-containing heterocyclic ring; or $R_1$ and $R_2$, $R_2$ and $R_3$, or $R_3$ and $R_4$ may combine to form a 5- or 6-membered heterocyclic ring; provided at least one of $R_1$ to $R_4$ is a 5- or 6-membered nitrogen-containing heterocyclic ring, an alkyl group or aryl group substituted with an amino group, an alkyl group substituted with a nitrogen-containing heterocyclic ring, or $R_1$ and $R_2$, $R_2$ and $R_3$, or $R_3$ and $R_4$ form a 5- or 6-membered nitrogen-containing heterocyclic ring having at least two nitrogen atoms.

DETAILED DESCRIPTION OF THE INVENTION

Preferably, the emulsion of this invention is prepared by a process which comprises reacting a water-soluble silver salt with a water-soluble halide within a liquid reaction medium (e.g., an aqueous solution of hydrophilic colloid) containing a silver halide solvent of the formula (I).

The silver halide solvent of the formula (I) may be added in any step of the emulsion making process until the final size and shape of the silver halide grains is determined. For example, the solvent of the formula (I) is added to a colloidal substance in which silver halide is precipitated. It may be added in combination with any of the water-soluble salts used to form silver halide such as water-soluble silver salts (e.g., silver nitrate) or water-soluble halides (e.g., potassium bromide, sodium chloride and other alkali metal halides). It may also be added between two or more steps of the emulsion making process, but must be added prior to physical ripening of the silver halide.

The emulsion of this invention can be prepared by any conventional method described in P. Glafkides, *Chimie et Physique Photographique*, (Paul Montel, 1967), G. F. Duffin, *Photographic Emulsion Chemistry*, (The Focal Press, 1966), or V. L. Zelikman et al., *Making and Coating Photographic Emulsions*, (The Focal Press, 1964).

The water-soluble silver salt may be reacted with the water-soluble halide by sequential mixing, simultaneous mixing or a combination of the two methods. One possible example of the simultaneous mixing is the "controlled double-jet method" which can maintain a constant pAg level in the liquid phase wherein silver halide is formed.

The emulsion of this invention is prepared at a temperature which is generally between about 30° and 90° C., at a pH which is selected at any value but is preferably between about 3 and 9, and at a pBr of less than about 3 (pAg varies with the temperature and is generally greater than 6.5, e.g., at 30° C. pAg is greater than 9.1 and at 90° C. pAg is greater than 6.8). Silver halide grains may be formed or ripened physically in the presence of cadmium salt, zinc salt, lead salt, thallium salt, iridium salt or complex salt of iridium, rhodium salt or complex salt of rhodium, or iron salt or complex salt of iron.

The silver halide in the silver halide emulsion of this invention may be any of silver bromide, silver iodide, silver chloride, silver chlorobromide, silver bromoiodide and silver chlorobromoiodide, and the preferred silver halide emulsion contains at least 50 mol% of silver bromide. The most effective emulsion of this invention is a silver bromide or silver bromoiodide emulsion, particularly one which contains less than about 10 mol% of silver iodide.

One of the important advantages of the present invention is that silver halide grains having a (100) plane are produced. These grains have a better color sensitizing effect, for example, in comparison to grains having a (111) plane.

The silver halide photographic emulsion prepared according to this invention provides good results when the average diameter of silver halide grains is between about 0.2 and 4 microns, preferably between about 0.2 and 2 microns, and more preferably between about 0.50 and 2 microns. The average diameter of silver halide grains can be measured by a conventional method, for example, the method described in *The Photographic Journal*, Vol. 79, pp. 330–338, 1939.

The interior and the surface layer of the silver halide grains may be different phases or one homogeneous phase. They may be such that a latent image is formed primarily on the surface or in the interior of the grains. An internal latent image type silver halide having different core and surface phases is particularly preferred.

The silver halide emulsion of this invention is coated on the support so that the amount of silver per square foot of the support is between about 50 and 600 mg.

The silver halide solvent used in this invention is a compound of the formula (I) below and it is a thiourea derivative having no hydrogen atom at the 1- or 3-position. The derivative is incapable of assuming the thiol structure and thus will not substantially produce silver sulfide even in the presence of silver ions and under alkaline conditions. The compound is a tetra-substituted thiourea and contains at least one amino group or nitrogen-containing heterocyclic ring:

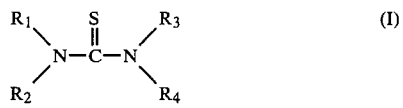

wherein $R_1$, $R_2$, $R_3$ and $R_4$ each represents a substituted or unsubstituted alkyl group (the alkyl moiety has preferably 1 to 5 carbon atoms, e.g., methyl group or ethyl group), a substituted or unsubstituted alkenyl group having 3 to 8 carbon atoms (e.g., allyl group), a substituted or unsubstituted aryl group having 6 to 8 carbon atoms (e.g., phenyl group or tolyl group), or a 5- or 6-membered nitrogen-containing heterocyclic ring; $R_1$, $R_2$, $R_3$ and $R_4$ may be the same or different and contain a total of up to 30 carbon atoms; $R_1$ and $R_2$, $R_2$ and $R_3$, or $R_3$ and $R_4$ when taken together may form a 5- or 6-membered nitrogen-containing heterocyclic ring, e.g., an imidazolidinethione, a piperidine, a piperazine, a morpholine or a pyrrolidine group, which nitrogen-containing heterocyclic ring may be substituted with, for example, an alkyl group (having preferably 1 to 5 carbon atoms, e.g., methyl group), a hydroxyl group or a carboxyl group.

The above defined alkyl group may be straight or branched. It may be substituted with, for example, a hydroxyl group, a carboxyl group, a sulfonic acid group, an amino group (e.g., a monoalkylamino group or a dialkylamino group containing 1 to 3 carbon atoms in the alkyl moiety and preferably a dialkylamino group), an alkoxy group wherein the alkyl residue has 1 to 5 carbon atoms, a phenyl group or a 5- or 6-membered nitrogen-containing heterocyclic ring (e.g., pyridine, imidazole or pyrazine).

The aryl group may be substituted with, for example, a hydroxyl group, a carboxyl group, a sulfonic acid group or an amino group (preferably a dialkylamino group).

The alkenyl group has preferably a total of 3 to 7 carbon atoms. The alkenyl group may be substituted with, for example, a hydroxyl group, a carboxyl group or a sulfonic acid group.

The 5- or 6-membered nitrogen-containing heterocyclic ring represented by $R_1$, $R_2$, $R_3$ or $R_4$ is preferably saturated and may contain an oxygen atom and/or a sulfur atom in addition to the nitrogen atom. The nitrogen-containing heterocyclic ring may bear a substituent such as an alkyl group (having 1 to 5 carbon atoms in the alkyl moiety, e.g., methyl group). Illustrative examples of the nitrogen-containing heterocyclic ring include a pyridine ring (e.g., 2-pyridine or 4-pyridine), a thiazole ring (e.g., 2-thiazole), an imidazole ring (e.g., 2-imidazole), a pyrazine ring (e.g., 2-pyrazine), and a 1,2,4-triazole ring (e.g., a 3-(1,2,4-triazole)).

The compound used in this invention is such that at least one of $R_1$ to $R_4$ of the formula (I) is a 5- or 6-membered nitrogen-containing heterocyclic ring, an alkyl or aryl group substituted with an amino group, an alkyl group substituted with a nitrogen-containing heterocyclic ring, or $R_1$ and $R_2$, $R_2$ and $R_3$, or $R_3$ and $R_4$ combine to form a 5- or 6-membered nitrogen-containing heterocyclic ring containing at least 2 nitrogen atoms. Examples of such compounds include salts thereof with mineral acids such as hydrochloric acid or salts thereof with organic acids such as acetic acid.

In the formula (I), it is preferred that $R_1$ to $R_4$ have a total of 20 carbon atoms or less. The substituent amino group is preferably a tertiary amino group (e.g., a dimethylamino group, or diethylamino group). Particularly preferred compounds are ones in which at least one of $R_1$ and $R_2$ and $R_3$ and $R_4$ combine to form a ring such as Compounds 1 and 4 below.

Examples of the compound that can be used in this invention include the following:

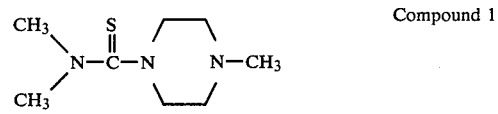

Compound 1

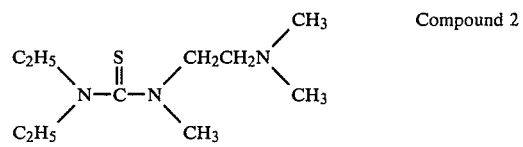

Compound 2

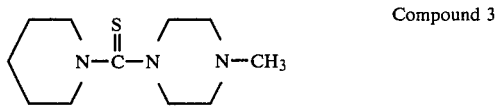

Compound 3

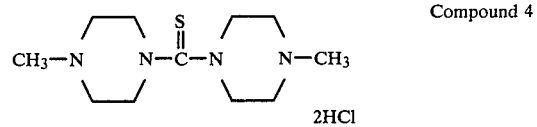

Compound 4

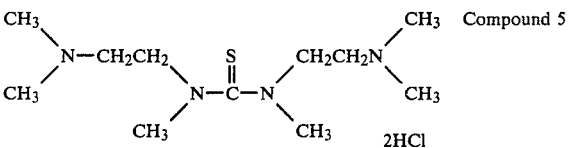

Compound 5

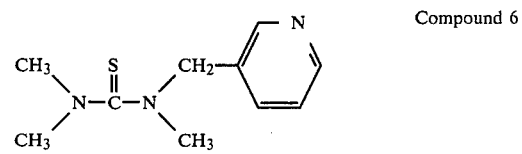

Compound 6

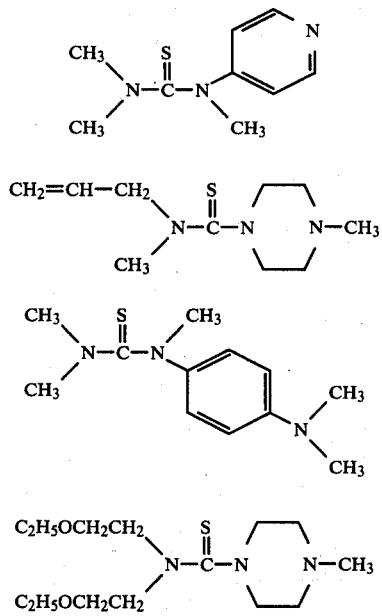

Compound 7

Compound 8

Compound 9

Compound 10

These compounds are synthesized by well known methods which are illustrated by the following preparations.

SYNTHESIS EXAMPLE 1

Synthesis of Compound 1

To 50 g (0.5 mol) of 1-methylpiperazine in 100 ml of benzene was added 24.8 g (0.25 mol) of dimethylthiocarbamoyl chloride in 100 ml of benzene, and the mixture was heated to 50° to 60° C. under stirring. Two hours later, the mixture was cooled, the crystal precipitated was filtered off, the filtrate was concentrated, and the residue was distilled under vacuum. Compound 1 was distilled off at 132° to 134° C./0.8 mmHg in a yield of 23.5 g (62.6%).

| | Elemental Analysis: | | |
|---|---|---|---|
| | C | H | N |
| Calcd. (%) for | 51.30 | 9.15 | 22.43 |
| Found (%) | 51.28 | 9.22 | 22.51 |

Synthesis of Compound 4

To 96 g (0.96 mol) of 1-methylpiperazine in 200 ml of acetonitrile was added dropwise 25 g (0.22 mol) of thiophosgene in 50 ml of benzene under cooling with ice. After the addition, the mixture was heated to 70° to 75° C. and stirred for a period of 5 hours. The mixture was then cooled, the crystal precipitated was filtered off, and the filtrate was concentrated. The residue was dissolved in 300 ml of water and extracted with chloroform. The chloroform solution was dried with $Na_2SO_4$. Blowing HCl gas into the solution caused a white crystal to precipitate. The crystal was filtered off and recrystallized from methanol. Compound 4 having a melting point of 270° C. or more was provided in a yield of 32 g (46.7%).

| | Elemental Analysis: | | |
|---|---|---|---|
| | C | H | N |
| Calcd. (%) for | 41.90 | 7.67 | 17.77 |
| Found (%) | 41.72 | 7.83 | 17.67 |

The other compounds are synthesized as Compound 1 if they are asymmetric thioureas, and as Compound 4 if they are symmetric thioureas.

The silver halide solvent of the formula (I) is used in an amount that varies widely depending upon the effect desired, the properties of the compound utilized and so forth. Generally, it is used in an amount of from about $5 \times 10^{-6}$ mol to $5 \times 10^{-2}$ mol per mol of silver halide. The preferred amount is from about $1 \times 10^{-5}$ mol to $2.5 \times 10^{-2}$ mol per mol of silver halide.

Following the formation of the precipitate or physical ripening, the emulsion of this invention is cleaned of excess soluble salts by a suitable method such as the well known Nudel washing which gels the gelatin, or flocculation utilizing an inorganic salt comprising a polyvalent anion such as sodium sulfate, an anionic surfactant, an anionic polymer (e.g., sulfonated polystyrene), or a gelatin derivative (e.g., aliphatic acylated gelatin, aromatic acylated gelatin or aromatic carbamoylated gelatin). Illustrative preferred flocculation methods are described in U.S. Pat. Nos. 2,614,928, 2,618,556, 2,565,418 and 2,489,341.

The step of removing the soluble salts may be omitted, but it is preferred that the compound of the formula (I) used in this invention be substantially removed prior to chemical sensitization, e.g., by conventional washing such as Nudel washing method or flocculation method.

The silver halide emulsion of this invention is generally used after chemical sensitization, though it may be used as a "primitive" emulsion which is not chemically sensitized. Chemical sensitization is performed by a suitable method described in Glafkides, supra, Zelikman, supra, or H. Frieser ed., *Die Grundlagen der Photographischen Prozesse mit Silberhalogeniden*, (Akademische Verlagsgesellschaft, 1968). Illustrative sensitizing methods are the sulfur sensitization that uses a compound containing sulfur reactive with silver ion and activated gelatin, the reduction sensitization using a reducing material, and the nobel metal sensitization using gold and other noble metals, and these methods may be employed independently or in combination. Suitable sulfur sensitizers include thiosulfates, thioureas, thiazoles, rhodanines and other compounds. Illustrative sulfur sensitizers are described in U.S. Pat. Nos. 1,574,944, 2,410,689, 2,278,947, 2,728,668 and 3,656,955. Suitable reduction sensitizers include stannous salts, amines, hydrazine derivatives, formamidine sulfinate, and silane compounds. Illustrative reduction sensitizers are described in U.S. Pat. Nos. 2,487,850, 2,419,974, 2,518,698, 2,983,609, 2,983,610 and 2,694,637. The noble metal sensitization may employ sensitizers such as complex salts of gold and metals of Group VIII of the Periodic Table such as platinum, iridium, and palladium. Illustrative noble metal sensitizers are described in U.S. Pat. Nos. 2,399,083, 2,448,060 and British Patent 618,061.

The photographic emulsion of this invention may be spectrally sensitized with methine dyes or the like. Suitable dyes include a cyanine dye, merocyanine dye, complex cyanine dye, complex merocyanine dye, holopolar cyanine dye, hemicyanine dye, styryl dye and hemioxonol dye. Particularly useful dyes are cyanine dyes, merocyanine dyes and complex merocyanine dyes. The basic heterocyclic ring nucleus of these dyes may be any of the nuclei conventionally used in the cyanine dyes. Illustrative examples include a pyrroline nucleus, oxazoline nucleus, thiazoline nucleus, pyrrole nucleus, oxazole nucleus, thiazole nucleus, selenazole nucleus, imidazole nucleus, tetrazole nucleus and pyridine nucleus; nuclei having an alicyclic hydrocarbon ring fused to these nuclei; and nuclei having an aromatic hydrocarbon ring fused to these nuclei, such as an indolenine nucleus, benzindolenine nucleus, indole nucleus, benzoxazole nucleus, naphthoxazole nucleus, benzothiazole nucleus, naphthothiazole nucleus, benzoselenazole nucleus, benzimidazole nucleus and quinoline nucleus. These nuclei may be substituted on a carbon atom.

The nuclei having the ketomethylene structure that can be applied to the merocyanine dye or complex merocyanine dye include 5- or 6-membered heterocyclic ring nuclei such as a pyrazoline-5-one nucleus, thiohydantoin nucleus, 2-thioxazolidine-2,4-dione nucleus, thiazolidine-2,4-dione nucleus, rhodanine nucleus and thiobarbituric acid nucleus.

Illustrative useful sensitizing dyes are described in West German Pat. No. 929,080, U.S. Pat. Nos. 2,231,658, 2,493,748, 2,503,776, 2,519,001, 2,912,329, 3,655,394, 3,656,959, 3,672,897, 3,694,217, British Patent 1,242,588, and Japanese Patent Publication No. 14030/69.

These sensitizing dyes may be used independently or in combination. They are often used in combination for the purpose of amplified sensitization. Typical examples of the combination of the sensitizing dyes are described in U.S. Pat. Nos. 2,688,545, 2,977,229, 3,397,060, 3,522,052, 3,527,641, 3,617,293, 3,628,964, 3,666,480, 3,679,428, 3,703,377, 3,769,301, 3,814,609, 3,837,862, British Patent 1,344,281, and Japanese Patent Publication No. 4936/68.

In addition to the sensitizing dye, the emulsion may contain a dye that does not have spectral sensitizing activity or a substance that does not substantially absorb visible light and which provides the effect of amplified sensitization. Examples of such dye or substance include an aminostilbene compound substituted with a nitrogen-containing heterocyclic ring group (such as those described in U.S. Pat. Nos. 2,933,390 and 3,635,721), an aromatic organic acid/formaldehyde condensate (such as those described in U.S. Pat. No. 3,473,510), cadmium salts and azaindene compounds. Particularly useful combinations are described in U.S. Pat. Nos. 3,615,613, 3,615,641, 3,617,295 and 3,635,721.

The silver halide grains prepared according to this invention may be fogged to form a direct positive type emulsion. The silver halide grains prepared in the presence of a compound of the formula (I) may be doped with a metal ion in the form of an iridium salt, rhodium salt or lead salt to form a direct positive type emulsion having high photographic sensitivity. The grains may also be used to form a direct positive type emulsion that is not doped with metal ions. Fogging can be accomplished by treating the silver halide chemically or physically in the conventional manner.

In this invention, the fogging nucleus is advantageously provided by fogging the silver halide grains chemically, for example, by addition of an inorganic reducing compound such as stannous chloride or boron hydride, or by addition of an organic reducing compound such as a hydrazine compound, formalin, thiourea dioxide, polyamine compound, aminoborane or methyldichlorosilane. The reducing agent may be combined with the ion of a metal nobler than silver or with halide ion (see, for example, U.S. Pat. Nos. 2,497,875, 2,588,982, 3,023,102, 3,367,778, 3,501,307, British Pat. Nos. 707,704, 723,019, 821,251, 1,097,999, French Pat. Nos. 1,513,840, 739,755, 1,498,213, 1,520,822, 1,520,824, Belgian Pat. Nos. 708,563, 720,660, Japanese Patent Publication Nos. 13488/68, 40900/71). According to this invention, the silver halide grains may be fogged either before or after coating them onto the support.

If the emulsion of this invention is used in a direct positive type photographic material, it can contain not only the sensitizing dye defined above but also a desensitizer or desensitizing dye which is generally referred to as an electron acceptor. Illustrative useful electron acceptors are described in U.S. Pat. Nos. 3,023,102, 3,314,796, 2,901,351, 3,367,779, 3,501,307, 3,505,070, British Pat. Nos. 723,019, 698,575, 667,206, 748,681, 698,576, 834,839, 796,873, 875,887, 905,237, 907,367, 940,152, 1,155,404, 1,237,925, Japanese Patent Publication Nos. 13167/68, 14500/68 and 23515/71.

For the purpose of providing higher sensitivity or contrast or accelerating development, the photographic emulsion of this invention may contain polyalkylene oxide or ether, ester and amine derivatives thereof, thioether compounds, thiomorpholines, quaternary ammonium salt compounds, urethane derivatives, urea derivatives, imidazole derivatives and 3-pyrazolidones. Illustrative suitable additives are described in U.S. Pat. Nos. 2,400,532, 2,423,549, 2,716,062, 3,617,280, 3,772,021, 3,808,003.

The silver halide emulsion of this invention may contain an antifoggant or a stabilizer. Suitable compounds are described in *Product Licensing Index*, Vol. 92, p. 107 "Antifoggants and stabilizers".

The silver halide emulsion may contain a developing agent. Suitable developing agents are described in *Product Licensing Index*, Vol. 92, pp. 107–108 "Developing agents".

The silver halide can be dispersed in a colloid which can be hardened with an organic or inorganic hardener. Suitable hardeners are described in *Product Licensing Index*, Vol. 92, p. 108 "Hardeners".

The silver halide emulsion may contain a coating aid. Suitable coating aids are described in *Product Licensing Index*, Vol. 92, p. 108 "Coating aids".

The silver halide emulsion of this invention may contain a so-called color coupler. Suitable color couplers are described in *Product Licensing Index*, Vol. 92, p. 110 "Color materials".

The photosensitive material prepared by this invention may contain dyes in a photographic emulsion layer or other hydrophilic colloid layers as a filter dye or for anti-irradiation or for other purposes. Suitable dyes are described in *Product Licensing Index*, Vol. 92, p. 109 "Absorbing and filter dyes".

The silver halide photographic emulsion may also contain an antistatic agent, plasticizer, matting agent, lubricant, U.V. absorber, fluorescent brightening agent or aerial fog inhibitor.

The silver halide emulsion of this invention may contain a vehicle as described in *Product Licensing Index*, Vol. 92, p. 108 "Vehicles", (December 1971).

The silver halide emulsion is coated onto the support together with other photographic layers, as required. Suitable coating methods are described in *Product Licensing Index*, Vol. 92, p. 109 "Coating procedures".

Suitable supports are described in *Product Licensing Index*, Vol. 92, p. 108 "Supports".

The silver halide photographic emulsion of this invention can be used in various applications such as a color positive emulsion, as a color paper emulsion, as a color negative emulsion, as a color reversal emulsion (which may or may not contain a coupler), as an emulsion of a plate making photosensitive material (e.g., a lith film), as an emulsion in a photosensitive material suitable for CRT display, as an emulsion in a photosensitive material for X-ray recording (particularly, a direct and indirect photosensitive material used with a fluorescent screen), as an emulsion used in the colloid transfer process (described in, e.g., U.S. Pat. No. 2,716,059), as an emulsion used in a silver salt diffusion transfer process (described in, e.g., U.S. Pat. Nos. 2,352,014, 2,543,181, 3,020,155 and 2,861,885), as an emulsion used in the color diffusion transfer process (described in, e.g., U.S. Pat. Nos. 3,087,817, 3,185,567, 2,983,606, 3,253,915, 3,227,550, 3,227,551, 3,227,552, 3,415,644, 3,415,645, 3,415,646, *Research Disclosure*, Vol. 151, 15162, pp. 75–87, November, 1976), as an emulsion used in the imbibition transfer process (described in, e.g., U.S. Pat. No. 2,882,156), as an emulsion used in the silver dye bleach process (described in, e.g., Friedman, *History of Color Photography*, Chap. 24, American Photographic Publishers Co., 1944, and *British Journal of Photography*, Vol. 111, pp. 308–309, Apr. 7, 1964), as an emulsion used in direct positive type photosensitive material (described in, e.g., U.S. Pat. Nos. 2,497,875, 2,588,982, 3,367,778, 3,501,306, 3,501,305, 3,672,900, 3,477,852, 2,717,833, 3,023,102, 3,050,395, and 3,501,307), as an emulsion used in heat development type photosensitive materials (described in, e.g., U.S. Pat. Nos. 3,152,904, 3,312,550, 3,148,122, British Pat. No. 1,110,046), and as an emulsion used in physical development type photosensitive materials (described in, e.g., British Pat. Nos. 920,277 and 1,131,238).

The emulsion of this invention is advantageously used as an emulsion for multilayered coupler-in-emulsion type color film, particularly color reversal film or color negative film or as an emulsion for black-and-white negative film (black-and-white high sensitivity negative film or micro negative film), or as an emulsion for color diffusion transfer process, or as an emulsion used in direct positive type photosensitive material.

Exposure may be carried out in the conventional manner. Thus, natural light (sunlight), tungsten lamp, fluorescent lamp, mercury lamp, xenon arc lamp, carbon arc lamp, xenon flash lamp, CRT flying spot, and other known light sources may be employed. The exposure time may vary over a very wide range: exposure for 1/1,000 second to one second as with the conventional camera, exposure for a period shorter than 1/1,000 second, such as 1/10$^4$ to 1/10$^6$ second as with a xenon flash lamp or CRT, or exposure for a period longer than 1 second. If necessary, a color filter may be used to control the spectral energy distribution of the light used for exposure. Exposure may be performed with a light emitted from a fluorescent substance excited by electron beam, X-ray, gamma-ray or alpha-ray.

The photosensitive material prepared in accordance with this invention may be subjected to any of the conventional methods of photographic processing. Illustrative methods are described in *Product Licensing Index*, Vol. 92, p. 110 "Processing".

One specific embodiment of this invention relates to a process for preparing a silver halide emulsion of relatively coarse silver halide grains in the presence of a silver halide solvent of the formula (I). The silver halide grains of the emulsion have an average diameter which is preferably greater than about 0.2 micron, and more preferably greater than about 0.5 micron.

Another embodiment of this invention relates to a direct positive type photographic emulsion having fogged silver halide grains whose average diameter is greater than 0.2 micron.

Still another embodiment of this invention relates to a novel photographic emulsion having silver halide grains doped with metal ion and having an average diameter greater than 0.2 micron.

A further embodiment of this invention relates to a novel photographic emulsion having cubic silver halide grains of narrow size distribution in a low pBr (high pAg) region.

Still another embodiment of this invention relates to a core/shell type, internal latent image type emulsion having high photographic sensitivity.

This invention is now described in greater detail by reference to the following examples which are given here for illustrative purposes only and are by no means intended to limit the scope of the invention.

EXAMPLE 1

| Solution I | |
|---|---|
| Gelatin | 30 g |
| H$_2$O | 440 cc |
| Potassium Bromide | 6 g |
| Solution II | |
| Silver Nitrate | 200 g |
| H$_2$O | 900 cc |
| Solution III | |
| Potassium Bromide | 140 g |
| H$_2$O | 900 cc |

To Solution I kept at 75° C. were added Solutions II and III under vigorous stirring. The emulsion had an initial pBr of about 0.94 and a final pBr of about 1.65. The emulsion was washed with water in a conventional manner. The resulting emulsion is designated A.

The procedure of preparing emulsion A was repeated except that prior to precipitation of silver halide, $3 \times 10^{-4}$ mol of Compound 1, a silver halide solvent of the formula (I), was added to the aqueous gelatin solution. The resulting silver bromide photographic emulsion is designated B.

The procedure of preparing emulsion B was repeated except that Compound 1 was replaced by Compound 4. The resulting photographic emulsion is designated C.

The procedure of preparing emulsion A was repeated except that prior to precipitation of silver halide, $3 \times 10^{-4}$ mol of tetramethyl thiourea, one silver halide solvent described in Japanese Patent Application (OPI) No. 82408/78 (The term "OPI" as used herein refers to a "published unexamined Japanese patent application"), was added to the aqueous gelatin solution. The resulting emulsion is designated D. The procedure of preparing emulsion A was repeated except that prior to precipitation of silver halide, $3 \times 10^{-4}$ mol of 1-dimethylthiocarbamoyl piperidine, another silver halide solvent described in Japanese Patent Application (OPI) No. 82408/78, was added to the aqueous gelatin solution. The resulting emulsion is designated E. Table 1 below shows the shapes and grain size ranges of emulsions A, B, C, D and E as observed with an electron microscope.

TABLE 1

| Emulsion | Shape | Grain Size (μ) | Remarks |
| --- | --- | --- | --- |
| A | Triangular, hexagonal, circular tabular grains | 0.3–2.5 | Control |
| B | Cubic grains | 0.7–0.85 | Invention |
| C | Cubic grains | 0.7–0.85 | " |
| D | Octahedral grains | 0.7–0.85 | Comparison |
| E | Octahedral grains | 0.7–0.85 | " |

Table 1 clearly shows that Compounds 1 and 4 of this invention formed cubic grains in a low pBr region, but that the control compounds did not.

EXAMPLE 2

Silver iodobromide emulsions were prepared from a formulation which was the same as that of Example 1 except that Solution III contained potassium iodide in an amount equal to 1 mol% of silver nitrate. They were subjected to the same testing as Example 1 and produced the same results as Example 1.

EXAMPLE 3

Emulsions B and C of Example 1, and emulsion F prepared using ammonia as a silver halide solvent and having an average grain size equal to emulsions B and C were coated onto a cellulose acetate film support until the coating weights of silver and gelatin were 400 mg/ft$^2$, and 656 mg/ft$^2$, respectively. Each coated sample was exposed to a 400 lux tungsten light for a period of 1/10 second through an optical wedge, and thereafter developed with a surface developer X of the formulation below at 20° C. for a period of 10 minutes. The same method was used to measure the photographic sensitivity of each sample at a predetermined density (an optical density of 0.1) higher than the fog density. The results are set forth in Table 2 below from which it can be seen that emulsions B and C precipitated in the presence of the compound of the formula (I) had a far higher sensitivity than emulsion F.

| Formulation of Surface Developer X | |
| --- | --- |
| N-Methyl-p-aminophenyl Sulfate | 2.5 g |
| Ascorbic Acid | 10.0 g |
| Potassium Metaborate | 35.0 g |
| Potassium Bromide | 1.0 g |
| Water to make | 1 l |

TABLE 2

| Emulsion | Average Grain Size (μ) | Relative Sensitivity | Remarks |
| --- | --- | --- | --- |
| B | 0.8 | 251 | Invention |
| C | 0.8 | 237 | " |
| F | 0.8 | 100 | Comparison |

EXAMPLE 4

Emulsions B and F of Example 3 were subjected to both sulfur and gold sensitizations, coated onto a cellulose acetate film support in the manner of Example 3, and were tested for photographic sensitivity. The results are set forth in Table 3 below.

TABLE 3

| Emulsion | Sodium Thiosulfate (mg/Ag/mol) | Chloroauric Acid (mg/Ag/mol) | Relative Sensitivity | Remarks |
| --- | --- | --- | --- | --- |
| B | 1.96 | 1.96 | 170 | Invention |
| F | 1.96 | 1.96 | 100 | Comparison |

EXAMPLE 5

In accordance with the formulation of emulsion A described in Example 1 of U.S. Pat. No. 3,761,276, two core/shell type, internal latent image type emulsions G and H were prepared using Compound 1 and ammonia as a silver halide solvent, respectively. The core surface of each emulsion was chemically sensitized with 3.4 mg of sodium thiosulfate and 3.4 mg of chloroauric acid per mol of silver. The resulting emulsions were coated onto a cellulose acetate film support and exposed as in Example 3, and processed by a fog developer Y of the following formulation. The results are indicated in Table 4 below.

| Formulation of Fog Developer Y | |
| --- | --- |
| N-Methyl-p-aminophenol Sulfate | 5 g |
| Hydroquinone | 10 g |
| Sodium Sulfite | 10 g |
| Sodium Metaborate | 30 g |
| Potassium Hydroxide | sufficient amount to give developer Y a pH of 11.5 |
| p-Tolylhydrazine Hydrochloride | 0.1 g |
| 5-Methylbenzotriazole | 0.02 g |
| Water to make | 1 l |

TABLE 4

| Emulsion | Average Grain Size (μ) | Crystal Habit | Relative Sensitivity | $D_{min}$ | $D_{max}$ | Remarks |
| --- | --- | --- | --- | --- | --- | --- |
| G | 1.4 | 100 cube | 372 | 0.06 | 1.40 | Invention |
| H | 1.4 | 100 cube | 100 | 0.08 | 1.12 | Comparison |

Table 4 clearly shows that emulsion G precipitated in the presence of the compound 1 of this invention provided a higher photographic sensitivity than the comparison emulsion H.

While the invention has been described in detail and with reference to specific embodiments thereof, it will be apparent to one skilled in the art that various changes and modifications can be made therein without departing from the spirit and scope thereof.

What is claimed is:

1. A silver halide photographic emulsion containing silver halide grains formed in the presence of a silver halide solvent or a salt thereof of the formula (I):

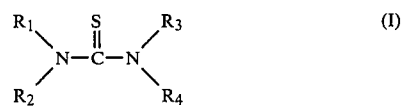

wherein $R_1$, $R_2$, $R_3$ and $R_4$ are each a substituted or unsubstituted alkyl group, a substituted or unsubstituted alkenyl group, a substituted or unsubstituted aryl group or a substituted or unsubstituted nitrogen-containing heterocyclic ring; $R_1$ and $R_2$, $R_2$ and $R_3$, or $R_3$ and $R_4$ when taken together may form a 5- or 6-membered heterocyclic ring; provided that at least one of $R_1$ to $R_4$ is a 5- or 6-membered nitrogen-containing heterocyclic ring, an alkyl group or aryl group substituted with an amino group, an alkyl group substituted with a nitrogen-containing heterocyclic ring, or $R_1$ and $R_2$, $R_2$ and $R_3$, or $R_3$ and $R_4$ form a 5- or 6-membered nitrogen-containing heterocyclic ring containing at least two nitrogen atoms.

2. The photographic emulsion of claim 1, wherein the total number of carbon atoms in $R_1$, $R_2$, $R_3$ and $R_4$ is not greater than 30.

3. The photographic emulsion of claim 1, wherein said silver halide contains at least 50 mol% silver bromide.

4. The photographic emulsion of claim 1, wherein said emulsion is a silver bromide or silver bromoiodide emulsion containing less than 10 mol% silver iodide.

5. The photographic emulsion of claim 1, wherein said silver halide has an average grain size of about 0.2 to 4μ.

6. The photographic emulsion of claim 1, wherein said silver halide has a grain size of about 0.5 to 2μ.

7. The photographic emulsion of claim 1, wherein said silver halide solvent is 1-dimethylthiocarbamoyl-4-methyl piperazine.

8. In a process for preparing a silver halide photographic emulsion, the improvement which comprises preparing silver halide grains in the presence of a silver halide solvent of the formula (I):

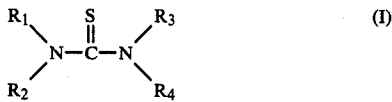

wherein $R_1$, $R_2$, $R_3$ and $R_4$ are each a substituted or unsubstituted alkyl group, a substituted or unsubstituted alkenyl group, a substituted or unsubstituted aryl group or a substituted or unsubstituted nitrogen-containing heterocyclic ring; $R_1$ and $R_2$, $R_2$ and $R_3$, or $R_3$ and $R_4$ when taken together may form a 5- or 6-membered heterocyclic ring; provided that at least one of $R_1$ to $R_4$ is a 5- or 6-membered nitrogen-containing heterocyclic ring, an alkyl group or aryl group substituted with an amino group, an alkyl group substituted with a nitrogen-containing heterocyclic ring, or $R_1$ and $R_2$, $R_2$ and $R_3$, or $R_3$ and $R_4$ form a 5- or 6-membered nitrogen-containing heterocyclic ring containing at least two nitrogen atoms.

9. The process of claim 8, wherein the total number of carbon atoms in $R_1$, $R_2$, $R_3$ and $R_4$ is not greater than 30.

10. The process of claim 8, wherein said silver halide solvent is used in an amount of about $5 \times 10^{-6}$ mol to $5 \times 10^{-2}$ mol per mol of silver halide.

11. The process of claim 8, wherein said silver halide solvent is used in an amount of about $1 \times 10^{-5}$ mol to $2.5 \times 10^{-2}$ mol per mol of silver halide.

12. The process of claim 8, wherein said compound of the formula (I) is removed prior to any chemical sensitization.

13. The photographic emulsion of claim 1, wherein said emulsion is a direct positive silver halide emulsion containing fogged silver halide grains.

14. The photographic emulsion of claim 1, wherein said emulsion is an internal latent image type emulsion.

15. The photographic emulsion of claim 14, wherein said internal latent image type emulsion is a core/shell type internal latent image type emulsion.

16. The photographic emulsion of claim 1, wherein said emulsion is chemically sensitized.

17. The photographic emulsion of claim 1, wherein said emulsion is spectrally sensitized.

18. The photographic emulsion of claim 1, wherein said silver halide grains are doped with a metal in the form of an iridium salt, a rhodium salt or a lead salt.

19. The process of claim 8, wherein said silver halide solvent is added in combination with any of the water-soluble salts used to form the silver halide.

20. The process of claim 8, wherein said silver halide solvent is added prior to physical ripening.

21. The photographic emulsion of claim 1, wherein said silver halide has a (100) plane.

22. The process of claim 8, wherein said silver halide has a (100) plane.

* * * * *